(12) United States Patent
Frodl et al.

(10) Patent No.: US 7,244,940 B2
(45) Date of Patent: Jul. 17, 2007

(54) GAS SENSOR ARRANGEMENT AND MEASURING METHOD FOR IMPROVING LONG-TERM STABILITY

(75) Inventors: Robert Frodl, München (DE); Hans-Dirk Loewe, München (DE)

(73) Assignee: Tyco Electronics Raychem GmbH, Ottobrunn (DE)

( * ) Notice: Subject to any disclaimer, the term of this patent is extended or adjusted under 35 U.S.C. 154(b) by 0 days.

(21) Appl. No.: 11/380,298

(22) Filed: Apr. 26, 2006

(65) Prior Publication Data
US 2006/0255278 A1 Nov. 16, 2006

(30) Foreign Application Priority Data
May 13, 2005 (DE) .................. 10 2005 022 288

(51) Int. Cl.
*G01J 5/02* (2006.01)
(52) U.S. Cl. ..................................... 250/343
(58) Field of Classification Search ............. 250/343
See application file for complete search history.

(56) References Cited

U.S. PATENT DOCUMENTS 6,843,102 B1 * 1/2005 Shulga et al. ............ 73/25.01

FOREIGN PATENT DOCUMENTS

| DE | 199 25 196 A 1 | 12/2000 |
|---|---|---|
| DE | 199 44 260 A1 | 4/2001 |
| EP | 0 616 207 A2 | 9/1994 |
| EP | 0 762 107 A1 | 3/1997 |
| EP | 1 605 251 A1 | 12/2005 |
| JP | 57190252 | 11/1982 |
| JP | 05223735 | 8/1993 |
| WO | WO 00/55603 | 9/2000 |

OTHER PUBLICATIONS

European Patent Office Search Report dated Jul. 13, 2006 for patent application No. EP 06 00 8441.

* cited by examiner

*Primary Examiner*—David Porta
*Assistant Examiner*—Mark R Gaworecki
(74) *Attorney, Agent, or Firm*—Barley Snyder LLC

(57) ABSTRACT

A gas sensor arrangement comprises a gas measuring chamber containing a gaseous analyte. First and second radiation sources emit radiation. The first radiation source operates as a measuring radiation source and the second radiation source operates as a reference radiation source. The radiation is directed through the gas measuring chamber and into a detector that generates an output signal depending on the presence of the gaseous analyte. A control device evaluates the output signal from the detector. The control device interchanges the operation of the first and second radiation sources after a predetermined service life.

19 Claims, 3 Drawing Sheets

GAS SENSOR ARRANGEMENT AND MEASURING METHOD FOR IMPROVING LONG-TERM STABILITY

FIELD OF THE INVENTION

The invention relates to a method for measuring the presence and/or the concentration of an analyte using a gas sensor arrangement and a gas sensor arrangement for performing the same.

BACKGROUND OF THE INVENTION

Gas sensor arrangements typically comprise a gas measuring chamber filled with a gaseous analyte, which contains at least one analyte to be measured. First and second radiation sources emit radiation toward a detector that detects the radiation and produces a mostly electric output signal, which depends on the presence and/or on the concentration of the analyte in the gas measuring chamber. The radiation sources are typically broadband radiation sources, such as incandescent lamps. These gas sensor arrangements are known for detecting the most varied types of analyte, for example, methane or carbon dioxide.

Examples of gas sensor arrangements are shown in EP 0616207 A2, WO 00/55603 A1 and DE 19925196 C2. These gas sensor arrangements are based on the concept that many polyatomic gases absorb radiation, in particular within the infrared wavelength range. This absorption occurs in a wavelength which is characteristic of the relevant gas, for example, at a wavelength of 4.24 µm in the case of carbon dioxide. The wavelength which is of interest is selected via an interference filter or grid. It is thus possible, using such gas sensor arrangements, to determine the presence of the analyte and/or the concentration of the analyte. The radiation intensity measured by the detector is a measurement of the concentration of the analyte according to the Beer-Lambert Law. This type of radiation generation is also referred to as a non-dispersive method or a non-dispersive infrared (NDIR) method in the case of an infrared-carbon dioxide analysis.

The detection of carbon dioxide is becoming increasingly important for applications in construction and automotive engineering. For example, in the case of heating and air conditioning, the content of the inside air is monitored so that when the concentration of carbon dioxide in the inside air increases a supply of fresh air is induced via a ventilation control system to increase energy efficiency. Additionally, since many modern air-conditioning systems, in particular in the automotive field, use carbon dioxide as a coolant, carbon dioxide gas sensors are needed to detect carbon dioxide leaks as a result of possible defects in the system. It has also been found that carbon dioxide concentration represents a basic indicator for the quality of inside air and is therefore highly significant as a control variable for air-conditioning systems.

Particularly in the automotive field, sensors of this type, however, must satisfy the highest requirements in terms of robustness, reliability and compactability. Long-term stability, i.e., a service life of about 10 years or more, is required. Because the specification values must be observed during the entire service life of the gas sensor arrangement, problems arise when the components of the gas sensor arrangement, in particular the radiation source and the switching electronics, age.

In order to counteract this problem, it is known to provide at least two radiation sources and two detectors in the gas sensor arrangement. One of the detectors measures the analyte and the other monitors the brightness of the radiation source using a different wavelength. With the aid of the second detector, the change detected in the brightness of the radiation source may be factored into a correction calculation. This known solution, however, suffers from the disadvantage that it is relatively complex.

Another known solution is shown in DE 199 25 196 C2. This gas sensor arrangement uses at least two radiation sources and only one detector. The first radiation source is used as a measuring radiation source and is used at a rate necessary for measurement. The second radiation source is used as a reference radiation source and is used less often and only for carrying out a comparative measurement and a referencing of the first radiation source. If the second radiation source is only used to produce a comparative measurement every x intervals compared to the measuring intervals, it may be assumed that the ageing of the second radiation source, which is lower by the factor x, is mapped onto the more severely ageing first radiation source. This known solution therefore provides a so-called burn-in phase with an extended service life for reducing an increased initial ageing.

This known solution has the disadvantage, however, that the first radiation source and the associated switching electronics age more rapidly by the factor x than the second radiation source and the associated switching electronics thereof. Thus, the final service life of the entire gas sensor arrangement is restricted by the service life of the first radiation source and the associated switching electronics.

BRIEF SUMMARY OF THE INVENTION

It is therefore an object of the invention to provide a gas sensor arrangement and a method for measuring the presence and/or the concentration of an analyte using the gas sensor arrangement wherein the gas sensor arrangement has an extended service life.

This and other objects are achieved by a gas sensor arrangement comprising a gas measuring chamber containing a gaseous analyte. First and second radiation sources emit radiation. The first radiation source operates as a measuring radiation source and the second radiation source operates as a reference radiation source. The radiation is directed through the gas measuring chamber and into a detector that generates an output signal depending on the presence of the gaseous analyte. A control device evaluates the output signal from the detector. The control device interchanges the operation of the first and second radiation sources after a predetermined service life.

This and other objects are further achieved by a method for measuring the presence and/or the concentration of an analyte in a gas sensor arrangement. The method comprises the steps of: providing a gas measuring chamber with a gaseous analyte; directing radiation from first and second radiation sources through the gas measuring chamber and into a detector; operating the first radiation source as a measuring radiation source and the second radiation source as a reference radiation source; generating an output signal depending on the presence of the gaseous analyte; evaluating the output signal from the detector; and interchanging the operation of the first and second radiation sources after a predetermined service life.

DETAILED DESCRIPTION OF THE INVENTION

Figure 1:
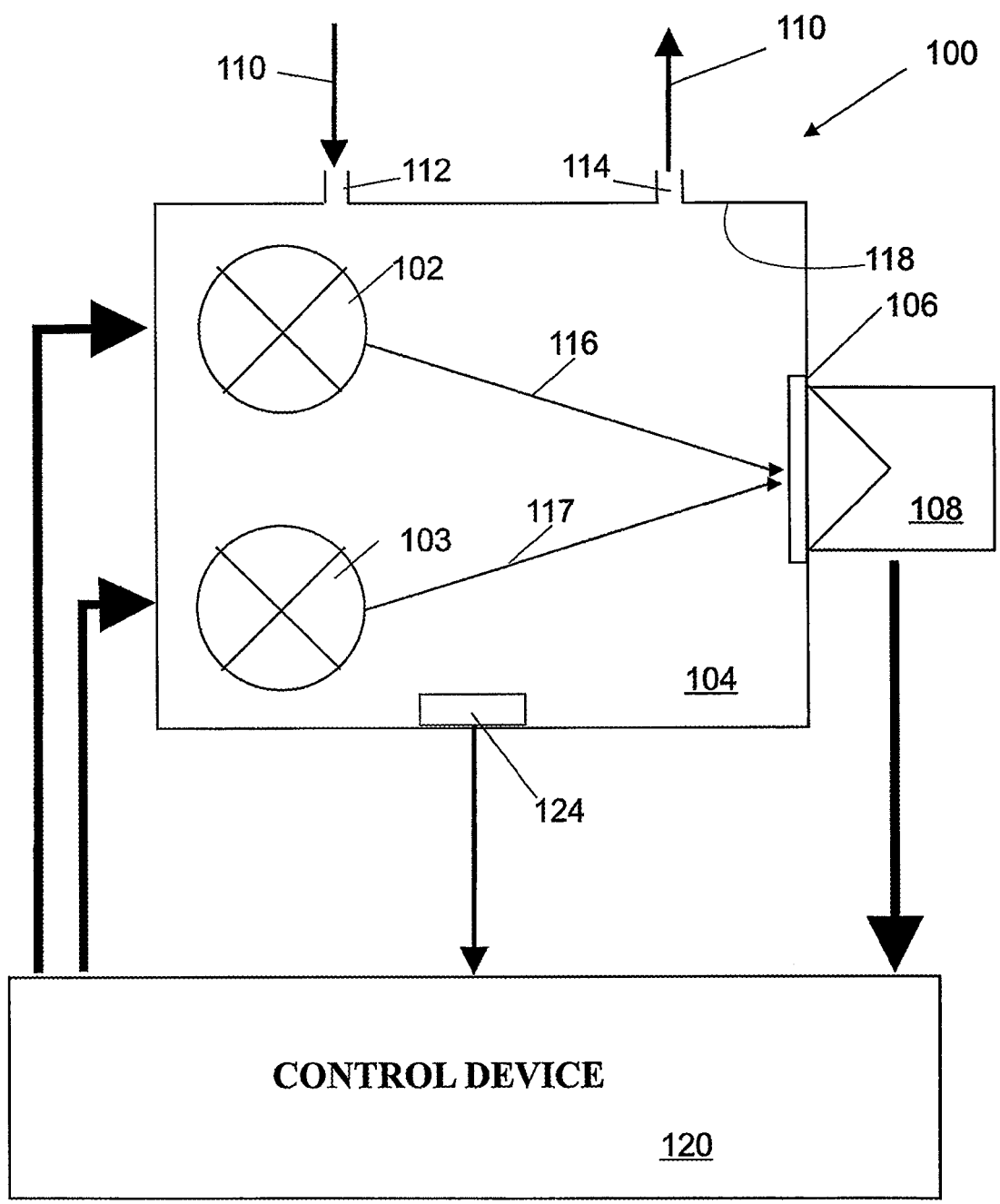
FIG. 1 is a block circuit diagram of a gas sensor arrangement according to a possible embodiment of the invention.

FIG. 1 shows a gas sensor arrangement 100 according to an embodiment of the invention. The gas sensor arrangement 100 may be, for example, a so-called NDIR sensor. The gas sensor arrangement 100 comprises a gas measuring chamber 104 containing first and second radiation sources 102, 103, respectively. The first and second radiation sources 102, 103 may be, for example, broadband infrared radiation sources, such as incandescent lamps. Radiation 116, 117 emitted from the first and second radiation sources 102, 103 is directed through the gas measuring chamber 104 through an optical filter 106 and into a detector 108. The first and second radiation sources 102, 103 are positioned such that beam paths of the emitted radiation 116, 117 have the same effective optical path length to the detector 108 or are positioned symmetrically to an axis of symmetry of the gas measuring chamber 104. A wall 118 of the gas measuring chamber 104 may be provided with a metal coating, such as a gold layer, that may be deposited on the wall 118, for example, by sputtering, vaporizing or electroplating, to reflect the radiation 116, 117 emitted by the first and second radiation sources 102, 103 thereby improving the efficiency of the gas sensor arrangement 100.

The gas measuring chamber 104 includes an inlet 112 and an outlet 114. A gaseous analyte 110 is pumped or diffused into the gas measuring chamber 104 through the inlet 112 and the outlet 114. The concentration of the analyte 110 may be determined electro-optically via the absorption of a specific wavelength in the infrared range. For example, for carbon dioxide, the characteristic wavelength is 4.24 µm. During this process, the optical filter 106 of the detector 108 only allows through the wavelength range in which the analyte 110 to be detected absorbs. Other gas molecules generally do not absorb any radiation in this wavelength range and thus do not influence the amount of the radiation 116, 117 that arrives at the detector 108. The emitted radiation 116, 117 may be pulsed or modulated in order to filter thermal background signals out of the desired signal.

Figure 4:
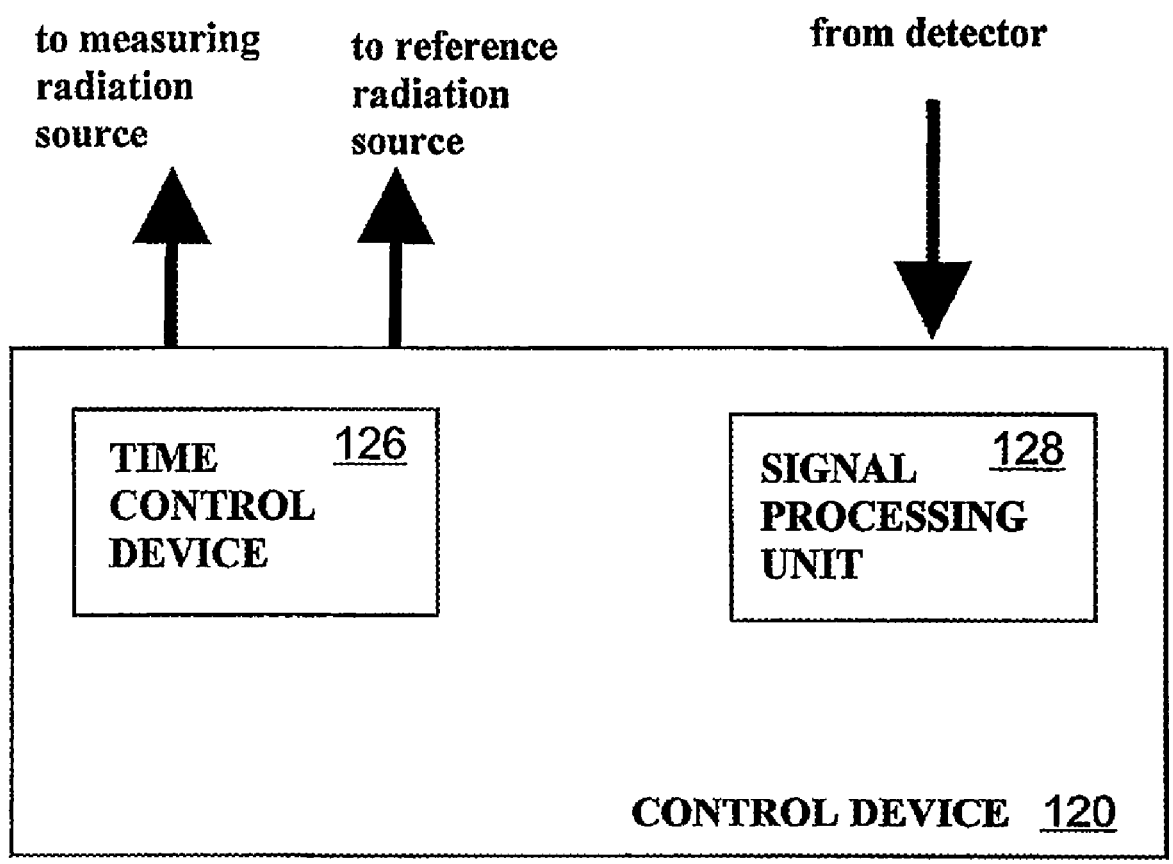
FIG. 4 is a schematic illustration of a control system according to a possible embodiment of the invention.

A control device 120 controls the first and second radiation sources 102, 103 and receives and further processes output signals from the detector 108. As shown in FIG. 4, the control device 120 comprises a time control device 126 which controls the pulsed operation of the first and second radiation sources 102, 103. A signal processing unit 128 receives the signals output by the detector 108 and processes them accordingly. In order to be able to eliminate background signals, for example, a frequency filter may be provided which is aligned with the pulse frequency during the measuring operation. The signal processing unit 128 may also supply signals to warning and indication devices based on the measurements. A temperature monitoring unit may also be connected to an optional temperature sensor 124, as shown in FIG. 1, to enable calculated correction of measurements due to temperature.

During a first referencing phase, the second radiation source 103 functions as a reference radiation source and the first radiation source 102 functions as a measuring radiation source. The second radiation source 103 is therefore switched on in time intervals to check the ageing state of the first radiation source 102. The control device 120 determines the age of the measuring radiation source by measuring deviations with respect to the output signals of the detector 108 when the second radiation source 103 is switched on compared to when the first radiation source 102 is switched on. If necessary, the control device 120 corrects the signals accordingly.

The control device 120 is configured such that after a predetermined service life of the gas sensor arrangement 100, the functions of the first radiation source 102 and of the second radiation source 103 are changed over in a second referencing phase, i.e., at the end of the predetermined service life. The first radiation source 102 then operates as the reference radiation source, and the second radiation source 103 operates as the measuring radiation source.

Figure 2:
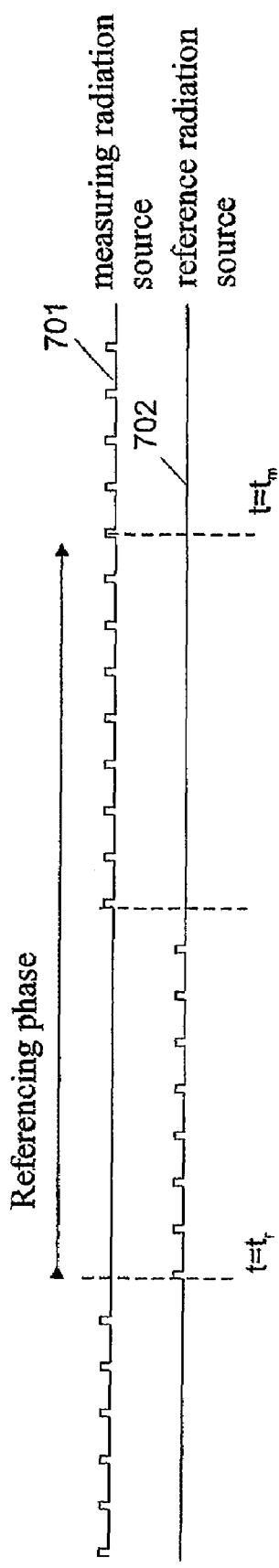
FIG. 2 is a time-dependency diagram of radiation pulses emitted during a first referencing phase from first and second radiation sources according to a possible embodiment of the invention.
Figure 3:
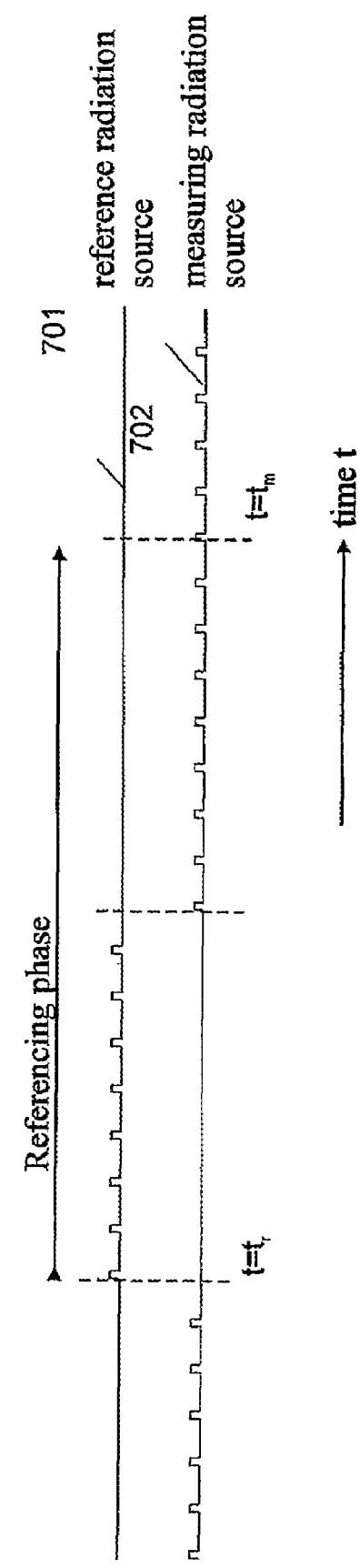
FIG. 3 is a time-dependency diagram of radiation pulses emitted during a second referencing phase from the first and second radiation sources according to a possible embodiment of the invention.

FIGS. 2-3 show the temporal sequence of the first and second radiation sources 102, 103 during the first and second referencing phases. FIG. 2 shows the pulsed operation of the first and second radiation sources 102, 103 during the first referencing phase where the first radiation source 102 is the measuring radiation source and the second radiation source 103 is the reference radiation source. FIG. 3 shows the pulsed operation of the first and second radiation sources 102, 103 during the second referencing phase where the second radiation source 103 is the measuring radiation source and the first radiation source 102 is the reference radiation source. The first radiation source 102 is shown as curve 701 and the second radiation source 103 is shown as curve 702.

As shown in FIG. 2, the first radiation source 102 emits radiation 116 in a substantially continuous and pulsed manner. In contrast thereto, the second radiation source 103 emits radiation pulses only intermittently during a part of the referencing phase, which commences with the triggering of the second radiation source 103. After approximately eight pulses of the second radiation source 103, for example, the first radiation source 102 is triggered again in order to initially ascertain comparative values for the correction procedure and to continue the measuring procedure. The referencing phase is then repeatedly re-enacted in longer time intervals.

As a result of the operation of the first and second radiation sources 102, 103 according to the pulse sequence shown in FIG. 2, the first radiation source 102 and the associated switching electronics age by a factor x, which is faster than the second radiation source 103 that is switched on less often. The first radiation source 102 thereby reaches a relatively more stable range than the second radiation source 103.

In FIG. 3, the first radiation source 102 is now used as the reference radiation source and the second radiation source 103 operates as the measuring radiation source. Since the first and second radiation sources 102, 103 are configured symmetrically and the control device 120 comprises, for example, embedded software, it is easy to interchange the function of the first and second radiation sources 102, 103. During this interchange, a referencing phase is preferably carried out as shown in FIG. 2. The ratio of sensitivities is determined and the reference radiation source is then re-used for measuring. In this way, it is possible for the measured values to become as stable as possible and to prolong the total life of the gas sensor arrangement 100.

The invention is based on the idea that in an arrangement comprising a measuring radiation source and a reference radiation source, the changes due to ageing decrease with an increasing service life. If the reference radiation source is operated by the factor x less often than the measuring radiation source, then conversely the measuring radiation source arrives, by the factor x faster than the reference radiation source, in a more stable range than the actual reference radiation source. It is therefore possible to observe the specification values for longer if, according to the invention, the functions of the first and second radiation sources 102, 103 are interchanged within the expected service life after an optimized time. Since the first and second radiation sources 102, 103 are constructed symmetrically and are usually controlled by so-called embedded software, this may be carried out in a particularly simple manner.

In addition to the improvement in long-term stability, this solution according to the invention also has the advantage of an obvious increase in the service life, because the operation of the first and second reference radiation sources 102, 103 and of the live switching electronics is divided during the entire service life. After the predetermined optimum service life, to interchange the first and second radiation sources 102, 103, a ratio is first of all advantageously determined between the sensitivity of the first and second radiation sources 102, 103. In this way it is particularly easy to achieve the transition from one radiation source to the other. If necessary, the interchanging step may also be repeated once or several times to achieve as uniform an ageing as possible of the complete system.

The foregoing illustrates some of the possibilities for practicing the invention. Many other embodiments are possible within the scope and spirit of the invention. For example, although the invention described herein is particularly effective when used for triggering a non-dispersive infrared radiation source for the measurement of carbon dioxide, the principles of the invention may also be applied to other radiation sources and to the analysis of other gases, insofar as the measuring radiation source and the reference radiation source are provided with substantially identical characteristics and are in a symmetrical arrangement, so that the interchange thereof is possible according to the principles of the invention. Additionally, although the gas sensor arrangement 100 described herein includes two radiation sources 102, 103 and one detector 108, any number of radiation sources and detectors may be used. Further, it is possible to provide other pulse sequences for the first and second radiation sources 102, 103 other than those described herein. It is, therefore, intended that the foregoing description be regarded as illustrative rather than limiting, and that the scope of the invention is given by the appended claims together with their full range of equivalents.

What is claimed is:

1. A gas sensor arrangement, comprising:
   a gas measuring chamber containing a gaseous analyte;
   first and second radiation sources emitting radiation, the first radiation source operating as a measuring radiation source and the second radiation source operating as a reference radiation source, the radiation being directed through the gas measuring chamber and into a detector that generates an output signal depending on the presence of the gaseous analyte; and
   a control device evaluating the output signal from the detector, the control device interchanging the operation of the first and second radiation sources after a predetermined service life.

2. The gas sensor arrangement of claim 1, wherein the measuring radiation source emits the radiation in a continuous and pulsed manner and the reference radiation source emits the radiation in an intermittently pulsed manner.

3. The gas sensor arrangement of claim 1, wherein an optical filter is arranged between the first and second radiation sources and the detector.

4. The gas sensor arrangement of claim 1, wherein a wall of the gas measuring chamber has a metal coating.

5. The gas sensor arrangement of claim 1, wherein the radiation to be detected is infrared radiation.

6. The gas sensor arrangement of claim 1, wherein the first and second radiation sources are incandescent lamps.

7. The gas sensor arrangement of claim 1, wherein the first and second radiation sources are positioned symmetrically to an axis of symmetry of the gas measuring chamber.

8. The gas sensor arrangement of claim 1, wherein the radiation emitted from the first radiation source and the radiation emitted from the second radiation source has the same optical path length to the detector.

9. The gas sensor arrangement of claim 1, further comprising a temperature sensor that monitors a temperature of the gas measuring chamber.

10. A method for measuring the presence and/or the concentration of an analyte in a gas sensor arrangement, comprising the steps of:
    providing a gas measuring chamber with a gaseous analyte;
    directing radiation from first and second radiation sources through the gas measuring chamber and into a detector;
    operating the first radiation source as a measuring radiation source and the second radiation source as a reference radiation source;
    generating an output signal depending on the presence of the gaseous analyte;
    evaluating the output signal from the detector; and
    interchanging the operation of the first and second radiation sources after a predetermined service life.

11. The method of claim 10, further comprising determining a ratio of the sensitivities for the first and second radiation sources after interchanging the operation of the first and second radiation sources after the predetermined service life.

12. The method of claim 10, wherein the measuring radiation source emits the radiation in a continuous and pulsed manner and the reference radiation source emits the radiation in an intermittently pulsed manner.

13. The method of claim 10, further comprising coating a wall of the gas measuring chamber with a metal.

14. The method of claim 10, further comprising providing an optical filter between the first and second radiation sources and the detector.

15. The method of claim 10, further comprising monitoring a temperature of the gas measuring chamber with a temperature sensor.

16. The method of claim 10, wherein the radiation to be detected is infrared radiation.

17. The method of claim 10, wherein the first and second radiation sources are incandescent lamps.

18. The method of claim 10, further comprising positioning the first and second radiation sources symmetrical to an axis of symmetry of the gas measuring chamber.

19. The method of claim 10, wherein the radiation emitted from the first radiation source and the radiation emitted from the second radiation source has the same optical path length to the detector.

* * * * *